(12) United States Patent
Xu et al.

(10) Patent No.: US 6,368,283 B1
(45) Date of Patent: Apr. 9, 2002

(54) METHOD AND APPARATUS FOR ESTIMATING SYSTOLIC AND MEAN PULMONARY ARTERY PRESSURES OF A PATIENT

(75) Inventors: Jingping Xu; Philippe Pibarot, both of Montréal; Louis-Gilles Durand, St-Jean-de-Matha, all of (CA)

(73) Assignees: Institut de Recherches Cliniques de Montreal; Universite Laval, both of (CA)

( * ) Notice: Subject to any disclaimer, the term of this patent is extended or adjusted under 35 U.S.C. 154(b) by 0 days.

(21) Appl. No.: 09/658,631

(22) Filed: Sep. 8, 2000

(51) Int. Cl.$^7$ .................................................. A61B 5/00
(52) U.S. Cl. ....................... 600/485; 600/586; 600/528
(58) Field of Search .................................. 600/481, 485, 600/500, 586, 528

(56) References Cited

U.S. PATENT DOCUMENTS 6,050,950 A   4/2000  Mohler ........................ 600/485
6,254,544 B1 * 7/2001  Hayashi ....................... 600/500

OTHER PUBLICATIONS

Rick A. Nishimura et al, Progress in Cardiovascular Diseases, vol. XXXVI, No. 4, (Jan./Feb.) 1994; pp 309–342 "Quantitative Hemodynamics by Doppler Echocardiography: A Noninvasive Alternative to Cardiac Catheterization".
T.S. Leung et al., IEEE Proc.–Sci. Meas. Technol., vol. 145, No. 6, Nov. 1998, pp. 285–290 "Analysis of the Second Heart Sound for Diagnosis of paediatric heart disease".
S. Agio et al., Acta Cardiologica, vol. XLV, 1990, 3, pp. 199–202—"Noninvasive Estimation of the Pulmonary Systolic Pressure from the Spectral Analysis of the Second Heart Sound".
Carlo Longhini et al., The American Journal of Cardiology, vol. 68, Aug. 1, 1991—"A New Noninvasive Method for Estimation of Pulmonary Arterial Pressure in Mitral Stenosis".
Danmin Chen et al., Excerpta Medica, Inc. (Am J Cardiol 1996; 78:785–789)—"Estimation of Pulmonary Artery Pressure by Spectral Analysis of the Second Heart Sound".
Louis G. Durand et al., IEEE Transactions on Biomedical Engineering, vol., BME–33, No. 6, Jun. 1986, pp. 572–578 "Evaluation of FFT–Based and Modern Parametric Methods for the Spectral Analysis of Bioprosthetic Valve Sounds".
Herkole Sava et al., Proceedings, 19th International Conference, IEEE/EMBS Oct. 30–Nov. 2, 1997, Chicago, IL, USA, pp. 1316–1319—"Automatic Detection of Cardiac Cycle Based on an Adaptive Time Frequency Analysis of the Phonocardiogram".

\* cited by examiner

*Primary Examiner*—Robert L. Nasser
(74) *Attorney, Agent, or Firm*—Myers Bigel Sibley & Sajovec, P.A.

(57) ABSTRACT

The method of estimating systolic and mean pulmonary artery pressures of a patient, comprising the steps of (a) producing an electric signal $x_s(t)$ representative of heart sounds of the patient; (b) extracting second heart sound $S_2(t)$ from the signal produced in step (a); (c) extracting pulmonary and aortic components $P_2(t)$ and $A_2(t)$ from $S_2(t)$; (d) extracting a signal representative of mean cardiac interval; (e) correlating the pulmonary and aortic components $P_2(t)$ and $A_2(t)$ to obtain a cross correlation function; (f) measuring a splitting interval of the cross correlation function obtained in step (e); (g) producing a normalized splitting interval; and (h) estimating the systolic and mean pulmonary artery pressures by means of predetermined regressive functions. The present invention also relates to an apparatus for estimating systolic and mean pulmonary artery pressures of a patient.

9 Claims, 7 Drawing Sheets

METHOD AND APPARATUS FOR ESTIMATING SYSTOLIC AND MEAN PULMONARY ARTERY PRESSURES OF A PATIENT

FIELD OF THE INVENTION

The present invention relates to a method and apparatus for estimating systolic and mean pulmonary artery pressures of a patient. More specifically, the invention relates to converting the second heart sound signal contained in the phonocardiagram (PCG) into a pulmonary artery pressure estimate.

Pulmonary hypertension is a disease characterized by a progressive and sustained elevation of pulmonary artery pressure (PAP). Pulmonary hypertension is a common and serious complication of multiple cardiovascular and respiratory diseases. Acquired heart diseases lead to pulmonary hypertension by increasing pulmonary blood flow or by increasing pulmonary venous pressure, which is the most common cause of pulmonary hypertension. Congenital heart diseases associated with left-to-right shunts or abnormal communication between the great vessels are commonly associated with pulmonary hypertension and intrinsic pulmonary diseases, respiratory disorders, can also lead to pulmonary hypertension. Among the respiratory disorders are the syndrome of alveolar hypoventilation and sleep apnea. Among the intrinsic lung diseases are chronic obstructive pulmonary disease, chronic obstruction of upper airways, diseases limiting pulmonary expansion and respiratory distress syndrome.

The major consequence of pulmonary hypertension is right ventricular failure. Pulmonary hypertension is an important risk factor for morbidity and mortality in patients with cardiovascular or respiratory diseases. In patients with primary pulmonary hypertension, the median survival time is 2.8 years. With the onset of right ventricular failure, patient survival is generally limited to approximately 6 months. Early detection and regular monitoring of pulmonary hypertension in patients is therefore essential to adjust the medical treatment and determine optimal timing for surgery. As the options available for treating pulmonary hypertension have increased, the requirement for accurate and noninvasive methods allowing regular and safe estimation of PAP has also increased.

BACKGROUND OF THE INVENTION

Pulmonary hypertension is a serious cardiovascular dysfunction that is difficult to assess noninvasively. The PAP is usually measured using a pulmonary arterial catheter, Swan-Ganz catheter, in patients necessitating continuous monitoring of PAP. However, this method can cause several complications including lesions of the tricuspid valve, pulmonary valve, right ventricle, or pulmonary arteries, cardiac arrhythmia, dislodgment of a thrombus and infectious complications. This method is not recommended for repeated measurements, one time every week or month or 6 months depending on the evolution of the disease, because of the potential risks for the patient. Since regular evaluation of the PAP is very important for the follow up of the evolution of the disease and for the assessment of the efficacy of the treatment, noninvasive methods have been developed to allow frequent and accurate measurement of PAP.

Doppler echocardiography has been used for non-invasive estimation of the systolic PAP when tricuspid regurgitation can be detected as described by Nishimura, R. A. and Tajik, A. J., "Quantitative hemodynamics by Doppler echocardiography: A noninvasive alternative to cardiac catheterization," *Prog Cardiovasc Dis*, vol. 36, no. 4, pp. 309–342, 1994. The right ventricular systolic pressure can be calculated by adding the systolic pressure gradient across the tricuspid valve, measured by using continuous-wave Doppler to the estimated right atrial pressure. The atrial pressure is set to 14 mm Hg when the jugular venous pressure is normal or mildly elevated and 20 mm Hg when the jugular pressure is markedly elevated. When the jugular venous pressure is not available, it is recommend to use 5, 10, or 20 mm Hg to estimate the right atrial pressure depending on the degree of collapse of the inferior vena cava during inspiration. Recently, it was demonstrated that the right atrial pressure may be estimated with reasonable accuracy, r=0.75, using the tricuspid E/Ea ratio, where E is the tricuspid inflow velocity of the E wave measured by pulsed Doppler and Ea is the tricuspid annulus velocity measured by tissue Doppler at early diastole. Furthermore, the systolic pressure gradient across the pulmonary valve must be either negligible or estimated by Doppler and added to the tricuspid gradient and right atrial pressure. This noninvasive method can provide a high degree of correlation, $0.89 \leq r \leq 0.97$, and a standard error (SEE) varying from 7 to 12 mmHg in comparison with pulmonary artery catheterization, systolic PAP range: 20–160 mmHg.

However, the estimation of PAP by Doppler echocardiography has several important limitations. Firstly, the PAP cannot be estimated by Doppler in approximately 50% of patients with normal PAP, 10% to 20% of patients with elevated PAP, and 34% to 76% of patients with chronic obstructive pulmonary disease because of the absence of tricuspid regurgitation, a weak Doppler signal or poor signal-to-noise ratio. To improve the feasibility of the method in patients with a weak Doppler signal or poor signal-to-noise ratio, it is necessary to use contrast agent enhancement. Secondly, Doppler echocardiography tends to overestimate PAP in patients with normal PAP and significantly underestimates the PAP in patients with severe pulmonary arterial hypertension. One surprising limitation of the method is the relatively important standard error in contrast to the above mentioned high levels of correlation. This is due to various error contributions associated with the non zero angle of the Doppler beam with the flow, the approximate estimation of the right atrial pressure, the presence of obstruction and pressure loss in the right ventricular outflow tract or in the pulmonary valve in some patients, the non simultaneous measurement of Doppler and catheter measurements in some studies, the non simultaneous recording of peak atrial, peak ventricular and peak pulmonary arterial pressures in patients, the use of the modified Bernoulli equation, and other factors. Furthermore, Doppler echocardiography requires an expensive ultrasound system and a highly qualified technician. This method is thus not applicable for daily measurements of PAP in small clinics or at home.

Acoustic methods based on signal processing of the second heart sound, $s_2(t)$, have been studied for the estimation of PAP. The onset of the aortic, $A_2(t)$, and the pulmonary, $P_2(t)$, components of $S_2(t)$ marks the end of left and right ventricular systole and the beginning of left and right ventricular diastole, respectively. In patients with pulmonary hypertension, the intensity of $P_2(t)$ is accentuated and the delay of $P_2(t)$ in relation to $A_2(t)$ is increased due to the prolongation of right ventricular systole. Furthermore, the $A_2(t)$–$P_2(t)$ splitting time interval, SI, is indirectly proportional to the heart rate. Hence Leung et al. have underlined in "Analysis of the second heart sound for diagnosis of paediatric heart disease," *IEEE Proceedings Sci Meas Technol*, vol. 145, no. 6, pp. 285–290, 1998, the importance of normalizing the SI with respect to the duration of the cardiac cycle to obtain valuable diagnostic information. The normalized SI (NSI) has been found to be 3.3±1.8% in normal subjects whereas it was 5.2±1.1% in patients with pulmonary stenosis, a condition resulting in pressure overload of the right ventricle and 5.9±0.7% in patients with atrial septal defect, a condition resulting in volume overload of the right ventricle and the pulmonary circulation. However, the relationship between NSI and the pulmonary artery pressure has not been studied.

Several studies have been done on the relationship between the resonant frequency, Fp, and the quality factor, Q, of the spectrum of $P_2(t)$ and the systolic PAP measured by pulmonary artery catheterization. In the study of Aggio et al. "Noninvasive estimation of the pulmonary systolic pressure from the spectral analysis of the second heart sound," *Acta Cardiologica*, vol. XLV, no. 3, pp. 199–202, 1990, performed with 23 patients with mitral stenosis or high PAP, a significant correlation, r=0.96 and SEE<5 mmHg, was found between Fp and Q and the systolic PAP. In the study of Longhini et al. "A new noninvasive method for estimation of pulmonary arterial pressure in mitral stenosis," *American Journal of Cardiology*, vol. 68 pp. 398–401, 1991) a similar correlation, r=0.98 and SEE=4.2 mmHg, was found in 30 patients with mitral stenosis or a systolic PAP>34 mmHg. This study also showed significant correlations with the mean, r=0.88, and diastolic, r=0.87, PAPs.

There is a U.S. Pat. No. 6,050,950 issued to Mohler on Apr. 18, 2000 and entitled "Passive/non invasive systemic and pulmonary blood pressure measurement". In this patent, the systemic and pulmonary pressures are estimated by using a range of pressure/frequency curves collected from the second heart sound in a population sample. The main limitation of this approach is that, ideally, it requires a pre-calibration for each patient, i.e. the curves must be obtained invasively for each patient between the systemic pressure and the spectrum of $A_2(t)$ and between the pulmonary pressure and the spectrum of $P_2(t)$.

A retrospective study by Chen, D. et al. "Estimation of pulmonary artery pressure by spectral analysis of the second heart sound," *American Journal of Cardiology*, vol. 78 pp. 785–789, 1996, was performed by our group with 89 patients with a bioprosthetic heart valve to test and validate the method mentioned above by Longhini et al. and Aggio et al. in comparison with Doppler. However, it was not possible to reproduce the results of these studies because of the use of different PCG recording systems and patient populations. However, a different relationship was found by using additional features from the spectra of $S_2(t)$ and $A_2(t)$. The correlation was very good, r=0.84, SEE=5 mmHg and p<0.0001. The systolic PAP was obtained by using the following equation: PAP=47+0.68 Fp−4.4 Q−17 Fp/Fa−0.15 Fs, where Fs and Fa are the resonant frequencies of $S_2(t)$ and $A_2(t)$, respectively. Due to the dependence of the regressive equation on the patient population and PCG recording system, it became necessary to perform basic animal studies specifically designed to solve these limitations and find a relationship between $S_2(t)$ and the PAP that is sensitive and specific only to the PAP.

The above prior art revealed that it is difficult to convert the frequency content of $P_2(t)$ to provide an accurate estimate of the PAP that would be independent of the patient population and the PCG recording system.

An object of the present invention is to provide a noninvasive method and apparatus for estimating the systolic and pulmonary artery pressures of a patient with greater efficiency and precision than the methods and apparatus revealed by the prior art.

SUMMARY OF THE INVENTION

According to the present invention there is provided a method for estimating the systolic and mean pulmonary artery pressures of a patient, comprising the steps of:

(a) producing an electri c signal $x_s(t)$ representative of heart sounds of the patient;

(b) extracting second heart sound $S_2(t)$ from the signal produced in step (a);

(c) extracting pulmonary and aortic components $P_2(t)$ and $A_2(t)$ from $S_2(t)$;

(d) extracting a signal representative of mean cardiac interval from the signal produced in step (a);

(e) correlating the pulmonary and aortic components $P_2(t)$ and $A_2(t)$ to obtain a cross correlation function;

(f) measuring a splitting interval as the time of occurrence of the maximal value of the cross correlation function obtained in step (e);

(g) producing a normalized splitting interval by dividing the splitting interval obtained in step (f) by the mean cardiac interval obtained in step (d); and (h) estimating the systolic and mean pulmonary artery pressures by means of predetermined regressive functions, said predetermined regressive functions describing relationships between the normalized splitting interval and the systolic and mean pulmonary artery pressures.

According to the present invention, there is also provided an apparatus for estimating systolic and mean pulmonary artery pressures of a patient, comprising:

first producing means for producing an electric signal $x_s(t)$ representative of heart sounds of the patient;

first extracting means for extracting second heart sound $S_2(t)$ from the signal produced by the first producing means;

second extracting means for extracting pulmonary and aortic components $P_2(t)$ and $A_2(t)$ from $S_2(t)$ extracted by the first extracting means;

third extracting means for extracting a signal representative of mean cardiac interval from the signal produced by the first producing means;

correlating means for correlating the pulmonary and aortic components $P_2(t)$ and $A_2(t)$ to obtain a cross correlation function;

measuring means for measuring a splitting interval as the time of occurrence of the maximal value of the cross correlation function obtained by the correlating means;

second producing means for producing a normalized splitting interval by dividing the splitting interval obtained from the measuring means by the mean cardiac interval obtained from the third extracting means; and estimating means for estimating the systolic and mean pulmonary artery pressures by means of predetermined regressive functions, said predetermined regressive functions describing relationships between the normalized splitting interval and the systolic and mean pulmonary artery pressures.

Further objects, advantages and other features of the present invention will become more apparent upon reading of the following non-restrictive description of preferred embodiments thereof given for the purpose of exemplification only with reference to the accompanying drawings.

DETAILED DESCRIPTION OF THE DRAWINGS

It is an object of the present invention to provide a method and apparatus for using second heart sound $S_2(t)$ signals extracted from the PCG of both healthy and sick humans and animals to obtain a measurement of the systolic and mean PAPs. The PCG is an acoustic signal recorded non-invasively by an air-coupled or a contact microphone or a vibration transducer. The apparatus could be provided in a portable or ambulatory device made using state-of-the-art electronic components and electronic circuits integrated into a miniature housing. The apparatus could be worn for extended period of time without inconveniencing the patient.

Figure 1:
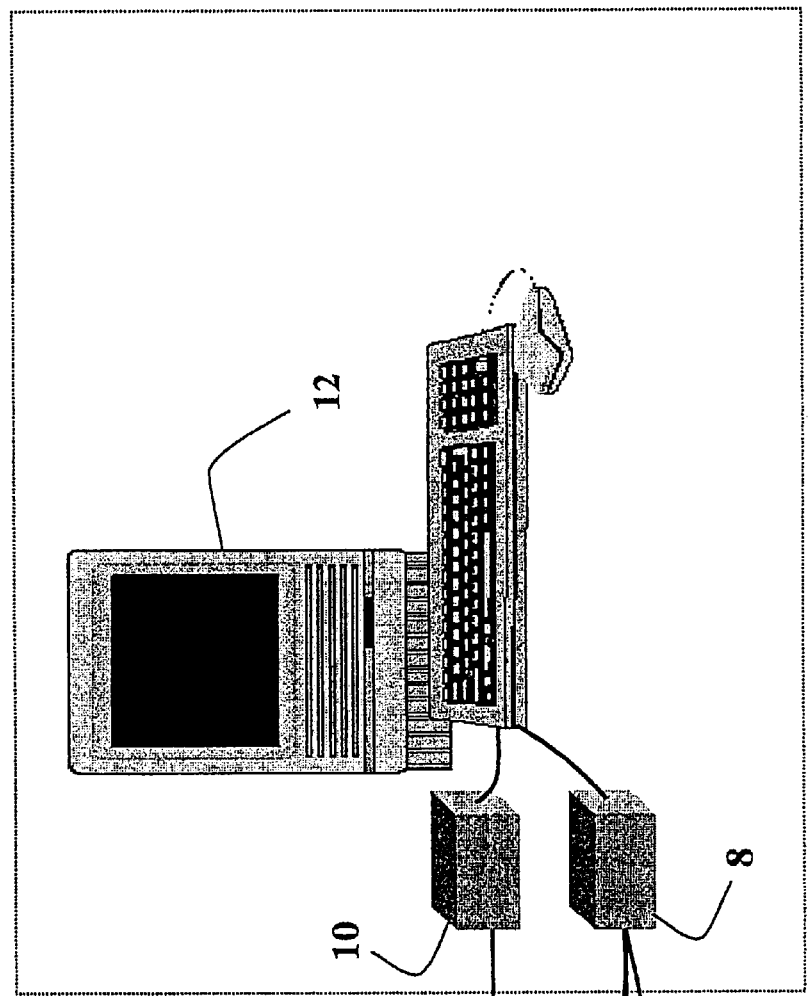
FIG. 1 is a schematic diagram illustrating an apparatus in accordance with the present invention within its environment.
Figure 2:
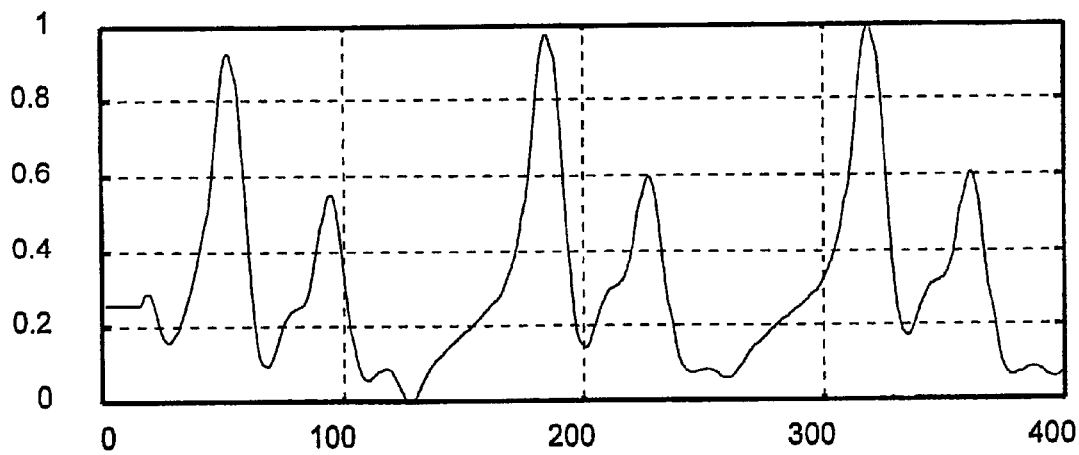
FIG. 2 shows a typical electrocardiogram (ECG) signal, amplitude versus time in milliseconds, recorded from one pig.
Figure 3:
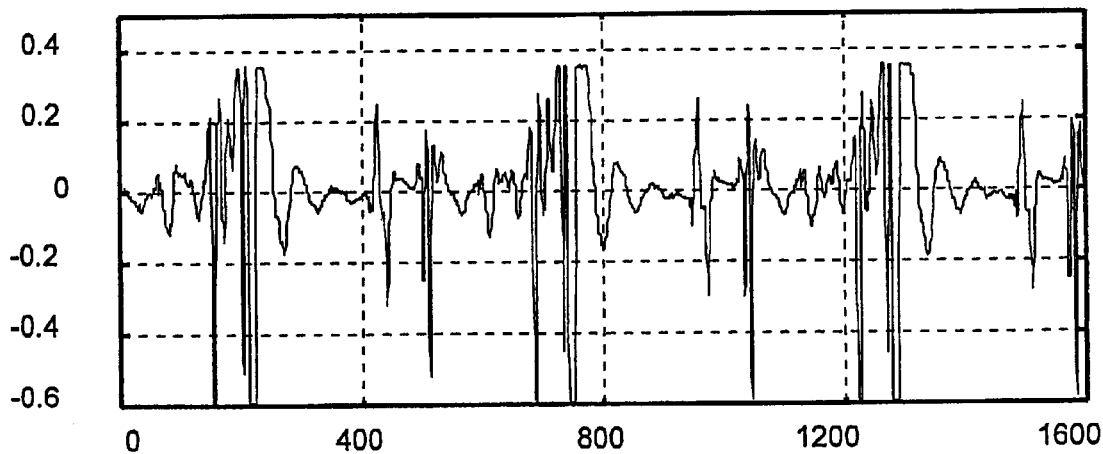
FIG. 3 shows a typical PCG signal, amplitude versus time in milliseconds, recorded from one pig.

A typical apparatus for performing the data acquisition and processing of the PCG and ECG signals is illustrated in FIG. 1. Examples of ECG and PCG signals are shown in FIGS. 2 and 3. Referring to FIG. 1, to record the ECG, three electrodes 4 are applied to the body surface of the subject 2 while the PCG signal is recorded using an air-coupled or a contact microphone 6. The ECG electrical signal is amplified through the use of a dedicated amplifier 8 and the PCG electrical signal is amplified through the use of a dedicated amplifier 10. The ECG and PCG signals are then digitized, and processed by a computer 12 which could be replaced by a hand held microcomputer or, preferably, by a dedicated portable or ambulatory microcomputer device.

Figure 4:
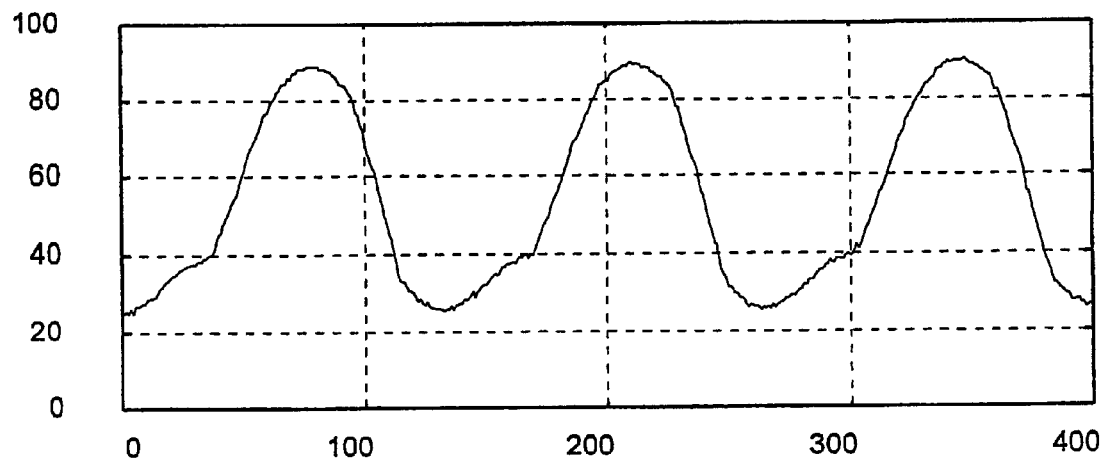
FIG. 4 shows a typical PAP signal, amplitude versus time in milliseconds, recorded from one pig.

FIG. 4 is provided here to illustrate the chronological relationship between the PCG shown in FIG. 3 and PAP signal. It was recorded by using a Swan-ganz catheter as described later in the experimental protocol.

Referring again to FIG. 1, an electric signal representative of the heart sounds of a patient is produced via the air-coupled or contact microphone or vibration transducer 6. This signal is amplified via a dedicated amplifier 10 and digitized by the computer 12 producing a digitized electric signal $x_s(t)$ which is representative of the heart sounds of a patient.

According to a preferred embodiment, the apparatus for estimating systolic and mean pulmonary artery pressures of a patient is embodied by means of a computer 12 which is provided with an appropriate software, electrodes 4, microphone 6 and dedicated amplifiers 8 and 10. The apparatus according to the present invention comprises a number of elements described below.

A first producing means is provided for producing an electric signal $x_s(t)$ representative of heart sounds of the patient. This first producing means is preferably embodied by the microphone 6 and the dedicated amplifier 10. Also included is a first extracting means for extracting the second heart sound $S_2(t)$ from the signal produced by the first producing means. Known in the art, there is a method to extract the second heart sound $S_2(t)$ such as the method described by Durand, L. G. et al. "Evaluation of FFT-based and modern parametric methods for the spectral analysis of bioprosthetic valve sounds," *IEEE Trans Biomed Eng*, vol. 33, no. 6, pp. 572–578, 1986). Additionally, a second extracting means is included for extracting the pulmonary and aortic components $P_2(t)$ and $A_2(t)$ from $S_2(t)$ extracted by the first extracting means. Furthermore, a third extracting means is implemented for extracting a signal representative of mean cardiac interval from the signal produced by the first producing means. Additionally, a correlating means is implemented for correlating the pulmonary and aortic components $P_2(t)$ and $A_2(t)$ to obtain a cross correlation function. Also, a measuring means for measuring a splitting interval as the time of occurrence of the maximal value of the cross correlation function obtained by the correlating means is implemented. Also provided for in this preferred embodiment is a second producing means for producing a normalized splitting interval by dividing the splitting interval obtained from the measuring means by the mean cardiac interval obtained from the third extracting means. Finally, an estimating means for estimating the systolic and mean pulmonary artery pressures by means of predetermined regressive functions, said predetermined regressive functions describing relationships between the normalized splitting interval and the systolic and mean pulmonary artery pressures. Preferably, the first extracting means, the second extracting means, the third extracting means, the correlating means, the measuring means, the second producing means and the estimating means are embodied by the computer 12.

By means of the apparatus as described above, it is possible to estimate the systolic and pulmonary artery pressures of a patient with greater efficiency and precision than the methods and apparatus as revealed by the prior art.

Preferably, the predetermined regressive functions have the form:

$$x = a + by^{1/n},$$

where y is the normalized splitting interval, $1 \leq n \leq 4$, x is either the systolic pulmonary artery pressure or the mean pulmonary artery pressure, and a and b are predetermined constants. The manner in which the preferred predetermined regressive functions are obtained will be described below in reference to FIGS. 10 and 11.

Preferably, the second extracting means described above comprises a number of elements also embodied by means of the computer 12. These elements are described in the following.

A first determining means is implemented for determining a Wigner-Ville distribution $W_s(t,f)$ in view of time t and frequency f of the signal $S_2(t)$ extracted by the first extracting means using the following function:

$$W_S(t, f) = \int_{-\infty}^{\infty} S_2\left(t + \frac{\tau}{2}\right) \cdot S_2^*\left(t - \frac{\tau}{2}\right) \cdot e^{-j2\pi f \tau} d\tau.$$

Additionally, a first filtering means is implemented for filtering $W_s(t,f)$ obtained from the first determining means. This uses the following function to obtain a masked time frequency representation $m_A(t,f)$ of the aortic component $A_2(t)$:

$$m_A(t,f) = W_s(t,f) \cdot \text{Mask}(t,f).$$

The Mask(t,f) is set to 1.0 around a first most dominant ridge, both in time and frequency, of $W_s(t,f)$, and 0.0 elsewhere. Also, a second determining means is included for determining the instantaneous frequency function $I_A(t)$ of the aortic component $A_2(t)$ using the following function:

$$I_A(t) = \frac{\int f \cdot m_A(t, f) df}{\int m_A(t, f) df}.$$

Furthermore, a third determining means is included for determining a phase function $\phi_A(t)$ of the aortic component $A_2(t)$ using the following function:

$$\varphi_A(t) = \int_{-\infty}^{t} I_A(t) dt.$$

Additionally, a fourth determining means is included for determining a low-frequency amplitude envelope $A_A(t)$ corresponding to the aortic component $A_2(t)$. The fourth determining means comprises a number of elements including: a determining means for determining an analytical form $S_{2C}(t)$ of the signal $S_2(t)$ using the following function:

$$S_{2C}(t) = S_2(t) + j \cdot S_{2H}(t)$$

where $S_{2H}(t)$ is the Hilbert Transform of $S_2(t)$; a multiplying means for multiplying $S_{2C}(t)$ by $\exp(-j\phi_A(t))$ to obtain $S_{2C}(t) \cdot \exp(-j\phi_A(t))$; and finally a filtering means for low-pass filtering the signal obtained from the multiplying means.

Also included in this preferred embodiment is a fifth determining means for determining the aortic component $A_2(t)$ using the function:

$$A_2(t) = A_A(t) \cdot \sin(\phi_A(t))$$

Additionally, a subtracting means is implemented for subtracting the signal $A_2(t)$ obtained by the fifth determining means from signal $S_2(t)$ obtained from the first extracting means to obtain a difference signal $x_D(t)$. Furthermore, a sixth determining means is implemented for determining a Wigner-Ville distribution $W_D(t,f)$ in view of time t and frequency f of the difference signal $x_D(t)$ by means of the following function:

$$W_D(t, f) = \int_{-\infty}^{\infty} x_D\left(t + \frac{\tau}{2}\right) \cdot x_D^*\left(t - \frac{\tau}{2}\right) \cdot e^{-j2\pi f \tau} d\tau.$$

Also, a second filtering means is included for filtering $W_D(t,f)$ obtained from the sixth determining means using the following function to obtain a masked time frequency representation $m_P(t,f)$ of the pulmonary component $P_2(t)$:

$$m_P(t,f) = W_D(t,f) \cdot \text{Mask}(t,f).$$

In the above Mask(t,f) is set to 1.0 around the most dominant ridge, both in time and frequency, of $W_D(t, f)$, and 0.0 elsewhere.

Additionally, a seventh determining means is implemented for determining the instantaneous frequency function $I_P(t)$ of the pulmonary component $P_2(t)$ by using the function:

$$I_P(t) = \frac{\int f \cdot m_P(t, f) df}{\int m_P(t, f) df}.$$

Also, an eighth determining means is included for determining the phase function $\phi_P(t)$ of the pulmonary component $P_2(t)$ by using the function:

$$\varphi_P(t) = \int_{-\infty}^{t} I_P(t)dt.$$

Furthermore, a ninth determining means is implemented for determining a low-frequency amplitude envelope $A_P(t)$ corresponding to the pulmonary component. The ninth determining means comprises a number of elements including: a tenth determining means for determining a analytical form $x_{DH}(t)$ of the signal $x_D(t)$ using the function:

$$x_{DC}(t)=x_D(t)+jx_{DH}(t)$$

where $x_{DH}(t)$ is the Hilbert transform of $x_D(t)$; a multiplying means for multiplying $x_{DC}(t)$ by $\exp(-j\phi_P(t))$ to obtain $x_{DC}(t)\cdot\exp(-j\phi_P(t))$; and finally a filtering means for low-pass filtering the signal obtained from the multiplying means.

Finally, the last element of this preferred embodiment of the second extracting means is an eleventh determining means for determining the pulmonary component $P_2(t)$ by using the following function:

$$P_2(t)=A_P(t)\cdot\sin\,(\phi_P)(t)).$$

Figure 5:
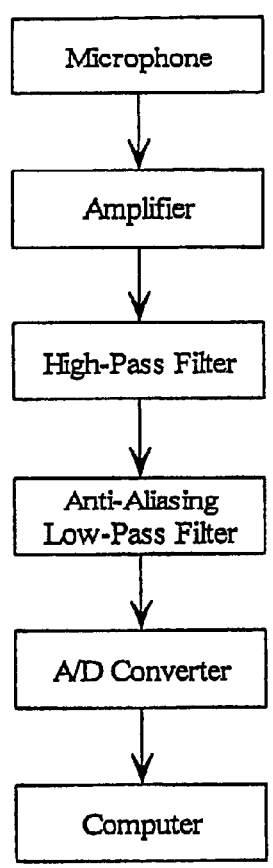
FIG. 5 is a flow chart showing the steps of the PCG signal acquisition.
Figure 6:
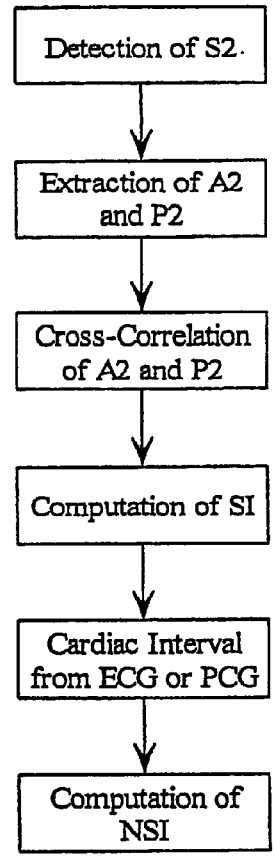
FIG. 6 is a flow chart showing the steps of the PCG signal processing.

Referring now to FIGS. 5 and 6, there are shown block diagrams of the PCG signal acquisition and processing stages. According to FIG. 5, the amplified PCG signal is high-pass filtered to eliminate low-frequency components not related to the PAP such as described by Chen, D. et al. "Estimation of pulmonary artery pressure by spectral analysis of the second heart sound," *American Journal of Cardiology*, vol. 78 pp. 785–789, 1996, such as cardiac motion, diaphragm motion and thoracic motion signals. According to Chen, D. et al. as mentioned above, the frequency range of the resonant frequency of $P_2(t)$ varied between 20 Hz and 200 Hz. Consequently, the overall frequency response of the PCG amplifier is limited to 300 Hz by using an integrated anti-aliasing $5^{th}$ order low-pass Butterworth filter. A 10-bit or 12-bit analog-to-digital converter controlled by computer is then used to digitized the PCG signal at a rate of 1000 samples per second. A similar process could be applied to the ECG signal. The digitized PCG signal is then processed in relationship to the QRS complex wave of the ECG which correspond to the complex electrical wave resulting from the electrical depolarization of the ventricles during the contraction of the heart, or directly to extract the $S_2(t)$ signal of each cardiac cycle, as well as to evaluate the duration of the cardiac interval as illustrated in FIG. 6. In the present application, this interval was computed from the ECG recorded on the body surface of animals. In the preferred embodiment, it could be derived from the digitized PCG by measuring the mean time interval from a series of two or more consecutive first heart sounds, $S_1(t)$ such as described by Sava, H. et al. "Automatic detection of cardiac cycle based on an adaptive time-frequency analysis of the phonocardiogram," *19th Annual International Conf IEEE-EMBS*, pp. 1316–1319, 1997. In one embodiment of the invention, the ECG signal, which is also used as a cardiac timing reference, could be replaced by a low frequency pulse signal recorded from the carotid artery or the brachial artery or directly from the thoracic area over the apex of the heart, the apexcardlogram, using low frequency vibration transducers. By low frequency pulse signal a frequency of less than 50 Hz is intended.

The procedure for signal processing of the PCG is illustrated in FIG. 6. A series of approximately ten consecutive $s_2(t)$ signals are detected from the digitized PCG, using either the QRS wave of the reference ECG signal such as described by Durand, L. G. et al. "Evaluation of FFT-based and modern parametric methods for the spectral analysis of bioprosthetic valve sounds," *IEEE Trans Biomed Eng*, Vol. 33, no. 6, pp. 572–578, 1986, or the method mentioned above and described by Sava et al. to identify $S_1(t)$ and $S_2(t)$. The $A_2(t)$ and $P_2(t)$ components are then extracted from the $S_2(t)$ signals. If $A_2(t)$ and $P_2(t)$ form two distinct and well separated waves in time, as shown in FIG. 3, $A_2(t)$ is identified as the first wave and utilized to compute the splitting interval (SI) between $A_2$ with $P_2(t)$ according to the correlation technique illustrated in FIGS. 8 and 9. If $A_2(t)$ and $P_2(t)$ are overlapping, the non linear transient chirp signal model of $A_2(t)$ and $P_2(t)$, as described below, is utilized and applied in the time-frequency domain to identify and separate $A_2(t)$ from $P_2(t)$, and then compute the SI.

In one embodiment, the cardiac interval is estimated by averaging the QRS wave interval of a series of 10 consecutive QRS waves from the ECOG signal or by averaging the $S_1(t)$-to-$S_1(t)$ interval of 10 consecutive $S_1(t)$, or the $S_2(t)$-to-$S_2(t)$ interval of 10 consecutive $S_2(t)$, on the PCG signal. The SI is then normalized to the cardiac interval as follows:

$$NSI(\%)=(100\times SI)/(\text{cardiac interval}) \quad (1)$$

Figure 7:
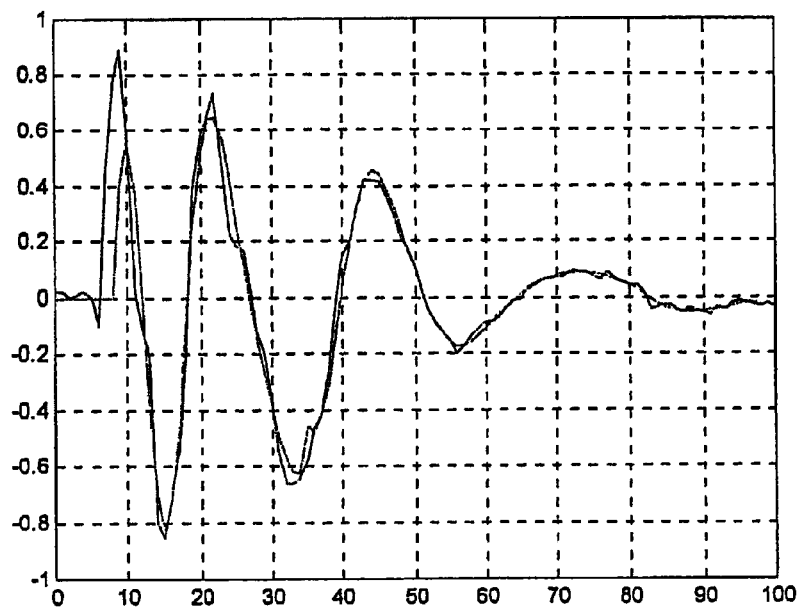
FIG. 7 is an example of a second heart sound with overlapping $A_2(t)$ and $P_2(t)$ components, amplitude versus time in milliseconds.
Figure 8:
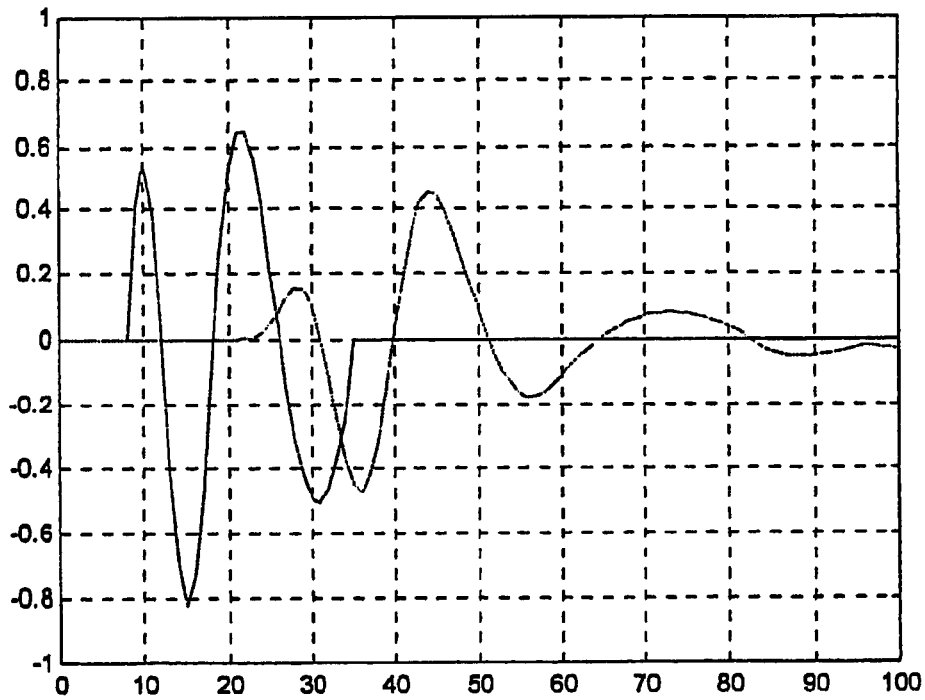
FIG. 8 shows the extracted $A_2(t)$ and $P_2(t)$ component from the $s_2(t)$ signal of FIG. 7, amplitude versus time in milliseconds.

The resulting value is inserted into the following two equations $$\text{Systolic } PAP=-21, 73+26, 35NSI^{0.5} \quad (2)$$

$$\text{Mean } PAP=-13, 73+19, 20NSI^{0.5} \quad (3)$$

to provide an estimate of the systolic and mean PAPs. These relationships are illustrated in FIGS. 7 and 8. They were obtained from an animal model of experimental pulmonary hypertension.

According to the present invention, there is also provided a method of estimating systolic and mean pulmonary artery pressures in a patient which commences with the producing of an electric signal $x_S(t)$ representative of the heart sound of the patient. The second heart sound $S_2(t)$ is extracted from $x_S(t)$ and then the pulmonary and aortic components, $P_2(t)$ and $A_2(t)$, are extracted from $S_2(t)$. A signal representative of mean cardiac interval is extracted from the signal $x_S(t)$. $P_2(t)$ and $A_2(t)$ are then cross correlated to obtain a cross correlation function which then allows the splitting interval to be determined as the time of occurrence of the maximal value of the cross correlation function. The splitting interval is then normalized by dividing it by the mean cardiac interval. Finally, the systolic and mean pulmonary artery pressures may be estimated by means of predetermined regressive functions. Preferably such functions have the form of x=a+$by^{1/n}$ such as those shown in FIGS. 10 and 11, where n=2.

$A_2(t)$ and $P_2(t)$ are each modeled as a narrow-band nonlinear chirp signal having a fast decreasing instantaneous frequency in time. Each component is defined by a pair of functions describing its instantaneous amplitude, such as its signal envelope, and its instantaneous phase, according to the following equation:

$$S_2(t)=A_A(t)\sin\,(\phi_A(t))+A_P(t-t_0)\sin\,(\phi_P(t))+N(t) \quad (4)$$

where $A(t)$ and $\phi(t)$ are the amplitude and the phase functions of each component identified by indices A for $A_2(t)$ and P for $P_2(t)$, $t_0$=SI, i.e. the splitting interval between $A_2(t)$ and $P_2(t)$, and $N(t)$ is the background noise of the digitized $S_2(t)$ signal, which includes thoracic noise, ambient noise and the electronic noise of the PCG amplifier and analog-to-digital converter.

The step of extracting aortic and pulmonary components $A_2(t)$ and $P_2(t)$ from $S_2(t)$ preferrably Comprises the following steps.

A Wigner-Ville distribution $W_S(t,f)$ of $S_2(t)$ is computed by using the following equation:

$$W_S(t, f) = \int_{-\infty}^{\infty} S_2\left(t + \frac{\tau}{2}\right) \cdot S_2^*\left(t - \frac{\tau}{2}\right) \cdot e^{-j2\pi f\tau} d\tau. \tag{5}$$

The resulting time-frequency distribution $W_s(t,f)$ is filtered by means of the following time-frequency function to obtain a masked time frequency representation, $m_A(t,f)$, of the aortic component $A_2(t)$:

$$m_A(t,f) = W_S(t,f) \text{ Mask } (t,f) \tag{6}$$

where:

Mask $(t,f) = 1.0$ around the dominant energy of the $A_2(t)$ trajectory in the time-frequency plane of $W_S(t,f)$, $= 0.0$ elsewhere in the time-frequency plane.

Here, the dominant energy of the $A_2(t)$ trajectory is defined as the first, both in time and frequency, most dominant ridge of $W_S(t,f)$.

The instantaneous frequency function $I_A(t)$ of the aortic component $A_2(t)$ is estimated by computing the following function:

$$I_A(t) = \frac{\int f \cdot m_A(t, f) df}{\int m_A(t, f) df}. \tag{7}$$

The phase function $\phi_A(t)$ of the aortic component $A_2(t)$ is computed by using:

$$\varphi_A(t) = \int_{-\infty}^{t} I_A(t) dt. \tag{8}$$

Once the phase function of $A_2(t)$ is obtained, the analytical form of the signal, $S_{2C}(t)$, is generated by using the Hilbert transform:

$$S_{2C}(t) = S_2(t) + jS_{2H}(t) \tag{9}$$

where $S_{2H}(t)$ is the Hilbert transform of $S_2(t)$, namely of the digitized $S_2(t)$ signal. The analytical signal is multiplied by the term $\exp(-J\phi_A(t))$ such that:

$$S_{2C}(t)\exp(-j\phi_A(t)) = A_A(t) + \{P_2(t-t_0) + N(t)\}\exp(j(\phi_P(t)) - \phi_A(t)). \tag{10}$$

Figure 15:
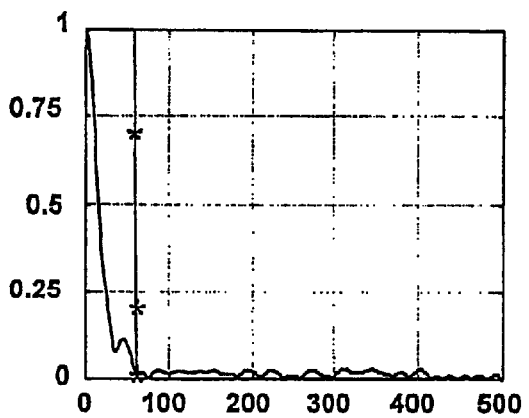
FIG. 15 shows the power spectrum (left curve) of the signal $s_{2C}(t) \exp(-j\phi_A(t))$ and the frequency response (vertical line located around 60 Hz with three stars representing the three transition coefficients) of the frequency filter used to separate the envelope $A_A(t)$ of the $A_2(t)$ signal from the signal $S_{2C}(t) \exp(-\phi_A(t))$.
Figure 16:
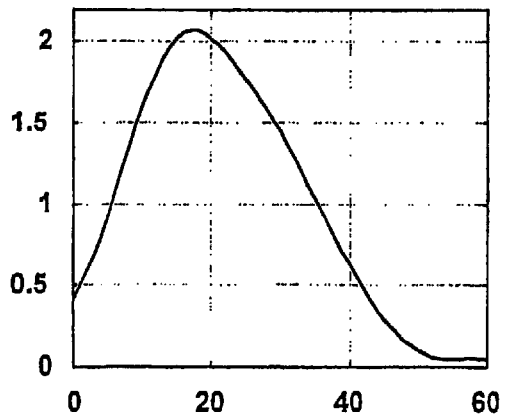
FIG. 16 shows the estimated $A_2(t)$ signal amplitude envelope, in amplitude versus time in milliseconds.
Figure 17:
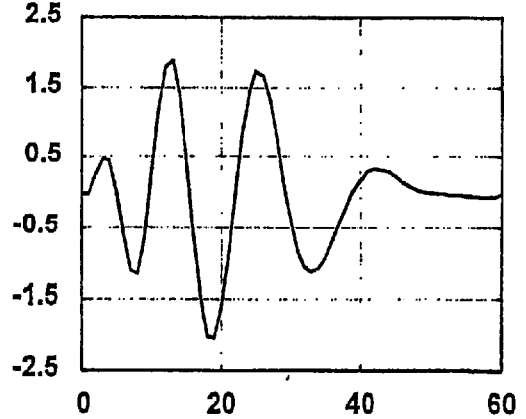
FIG. 17 shows the estimated $A_2(t)$ signal waveform, in amplitude versus time in milliseconds.

In this equation $\exp(-j\phi_A(t))$ means $e^{-j\phi A(t)}$ and $e=2.71828$. This dechirping operation generates the signal $A_A(t)$, which is a low-frequency component corresponding to the amplitude envelope of $A_2(t)$, and a phase modulated $P_2(t)$ signal including the background noise whose frequency is proportional to the splitting interval $t_0$ and the phase difference $(\phi_P(t) - \phi_A(t))$, as shown in FIG. 15. The amplitude envelope $A_A(t)$ of $A_2(t)$, as illustrated in FIG. 16, is obtained by applying a low-pass filter to the signal $S_{2C}(t)\exp(-j\phi_A(t))$ in the frequency domain with a cut-off frequency varying between 16 and 64 Hz, as illustrated in FIG. 15. The $A_2(t)$ component is then modeled by using:

$$A_2(t) = A_A(t) \sin(\phi_A(t)). \tag{11}$$

The $A_2(t)$ signal is synthesized using equation (11) and then subtracted from the digitized $S_2(t)$ signal after proper alignment using a correlation technique. The WVD of the difference signal $x_D(t)$ is computed according to the function:

$$W_D(t, f) = \int_{-\infty}^{\infty} x_D\left(t + \frac{\tau}{2}\right) \cdot x_D^*\left(t - \frac{\tau}{2}\right) \cdot e^{-j2\pi f\tau} d\tau \tag{12}$$

The time-frequency representation $W_D(t,f)$ is filtered by means of the following time-frequency function to obtain a masked time frequency representation $m_P(t,f)$ of the pulmonary component $P_2(t)$:

$$m_P(t,f) = W_D(t,f) \text{ Mask } (t,f) \tag{13}$$

where: Mask $(t, f) = 1.0$ around the dominant energy of the $P_2(t)$ trajectory in the time-frequency plane of $W_D(t, f)$ $= 0.0$ elsewhere in the time-frequency plane.

Here, the dominant energy of the $P_2(t)$ trajectory is defined as the most dominant ridge of $W_D(t,f)$ The instantaneous frequency function $I_P(t)$ of the pulmonary component $P_2(t)$ is computed by using the following function:

$$I_P(t) = \frac{\int f \cdot m_P(t, f) df}{\int m_P(t, f) df} \tag{14}$$

and its phase estimated $P_2(t)$ according to the function:

$$\varphi_P(t) = \int_{-\infty}^{t} I_P(t) dt. \tag{15}$$

The low-frequency amplitude envelope $A_P(t)$ corresponding to the pulmonary component $P_2(t)$ is then computed by using the analytical form $x_{DC}(t)$ of the signal $x_D(t)$ according to the following function:

$$x_{DC}(t) = x_D(t) + jx_{DH}(t) \tag{16}$$

where $x_{DH}(t)$ is the Hilbert transform of $x_D(t)$, namely of the difference signal. The analytical signal $x_{DC}(t)$ is multiplied by the term $\exp(-j\phi_P(t))$ such that:

$$x_{DC}(t)\exp(-j\phi_P(t)) = A_P(t) + N(t-t_0)\exp(j(\phi_P(t))). \tag{17}$$

The amplitude envelope $A_P(t)$ of $P_2(t)$ is obtained by applying a low-pass filter with a cutoff frequency varying between 16 and 64 Hz to the signal $x_{DC}(t)\cdot\exp(-j\phi_P(t))$ in the frequency domain in order to eliminate the terms $N(t-t_0)\cdot\exp(j(\phi_P(t)))$, which represents the residual modeling error signals of $A_2(t)$ and $P_2(t)$ including any background noise present in the original $S_2(t)$ signal.

Finally, the pulmonary component $P_2(t)$ is determined by means of the following function:

$$P_2(t) = A_P(t) \sin(\phi_P(t)). \tag{18}$$

Figure 21:
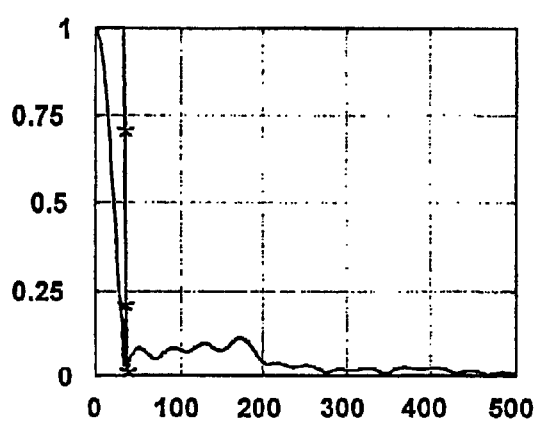
FIG. 21 shows the power spectrum (left curve) of the signal $x_{DC}(t) \exp(-\phi_P(t))$ and the frequency response (vertical line located around 40 Hz with three stars representing the three transition coefficients) of the frequency filter used to separate the envelope $A_p(t)$ of the $P_2(t)$ signal from the signal $x_{DC}(t) \exp(-\phi_p(t))$.
Figure 22:
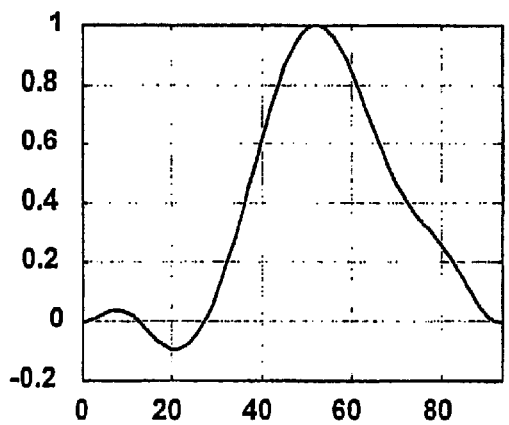
FIG. 22 shows the estimated $P_2(t)$ signal amplitude envelope, amplitude versus time in milliseconds.
Figure 23:
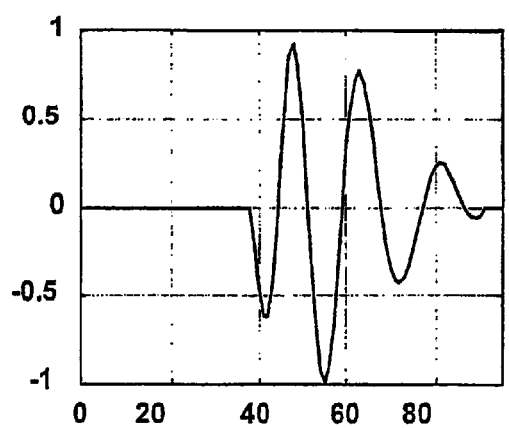
FIG. 23 shows the estimated $P_2(t)$ signal waveform, amplitude versus time in milliseconds.

The cut off frequency of the low-pass filters used to extract the amplitude function of $A_2(t)$ in equation (10) and that of $P_2(t)$ in equation (17) can be determined and applied directly in the frequency domain. Firstly, the signal $S_{2C}(t)\exp(-\phi_A(t))$ or $x_{DC}(t)\exp(-\phi_P(t))$ is transformed in the frequency domain using the Discrete Fourier Transform (DFT) and then its power spectrum computed and normalized to 1.0. Secondly, the bandwidth of the main low-frequency energy lobe of the power spectrum, see FIGS. 15 and 21, is determined by computing the frequency corresponding to 5% of the maximum energy of this lobe. This frequency is then considered as the cut off frequency of the low pass filter used to extract the amplitude envelope of the signal. Thirdly, filtering is applied in the frequency domain by using a filter that multiplies the real and imaginary parts of the DFT of the signal by 1.00 for those frequency bins below the cut off frequency, by 0.70 for the frequency bin corresponding to the cut off frequency, by 0.20 for the first frequency bin above the cut off frequency, by 0.02 for the second frequency bin above the cut off frequency, and by 0.00 for all other frequency bins above the cut off frequency, see FIGS. 15 and 21, also note the three transition coeffiecients (0.70, 0.20 and 0.02) which are identified by three stars on the frequency response of the low pass filter. Fourthly, the resulting DFT representation is transformed in the time domain by applying an inverse DFT.

Preferably, in view of the above, the low-pass filtering to extract $A_2(t)$ and $P_2(t)$ has the following steps.

First, the $S_2(t)$ signal or the difference signal $x_D(t)$ is transformed into frequency domain using a Discrete Fourier Transform and a transform obtained. Secondly, a power spectrum of the transform obtained in the first step is obtained. Thirdly, a main low-frequency energy lobe of the power spectrum is determined. Forth, the cut-off frequency as a frequency corresponding to 5% of energy of the main-low frequency energy lobe is determined. Fifth, frequency bins of the $S_2(t)$ signal or the difference signal $x_D(t)$ are determined using a Discrete Fourier Transform. Sixth, the real and imaginary parts of frequency bins which are below the cut-off frequency are multiplied by 1.00. Seventh, the real and imaginary parts of a frequency bin corresponding to the cut-off frequency are multiplied by 0.70. Eighth, the real and imaginary parts of the of a first frequency bin above the cut-off frequency are multiplied by 0.20. Ninth, the real and imaginary parts of the of a second frequency bin above the cut-off frequency are multiplied by 0.02.

Tenth, the real and imaginary parts of all other of the frequency bins which are above the cut-off frequency of the low pass filter are multiplied by 0.00. Finally, an inverse Discrete Fourier Transform is applied to the results of the sixth, seventh, eighth, ninth and tenth steps to obtain a representation in the time domain.

Figure 12:
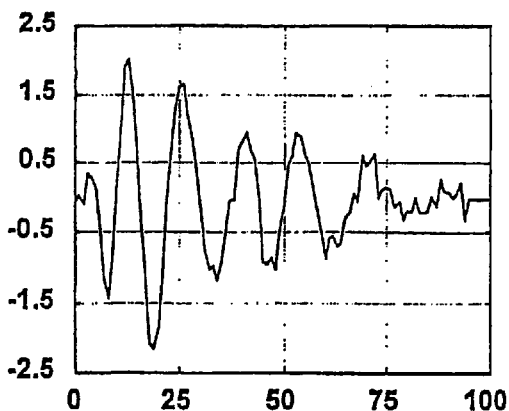
FIG. 12 shows a $S_2(t)$ signal, amplitude versus time in milliseconds.
Figure 13:
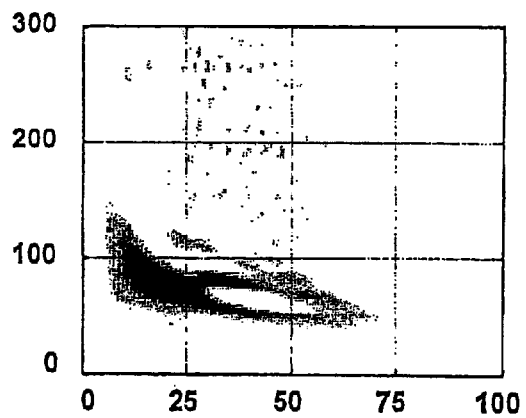
FIG. 13 shows the Wigner-Ville Distribution (WVD), frequency in Hertz versus time in milliseconds, of the $S_2(t)$ signal shown in FIG. 12.
Figure 14:
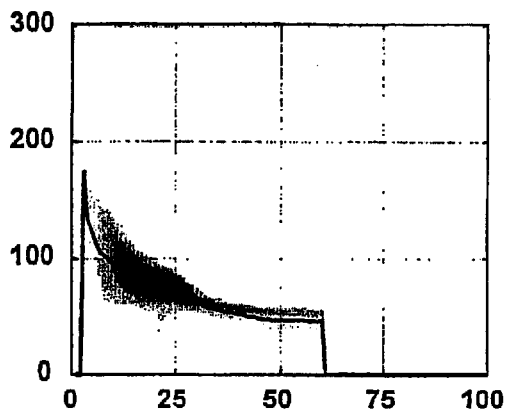
FIG. 14 shows the masked WVD, frequency in Hertz versus time in milliseconds, of the WVD of FIG. 13 with an estimated instantaneous frequency function of the $A_2(t)$ signal superimposed.
Figure 18:
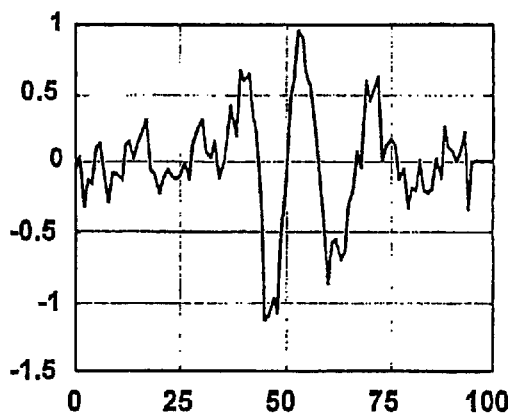
FIG. 18 shows the difference signal $x_D(t)$, in amplitude versus time in milliseconds, obtained by subtracting the estimated $A_2(t)$ signal from the $S_2(t)$ signal.
Figure 19:
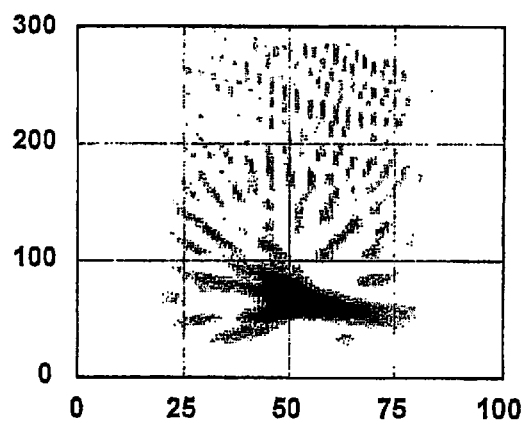
FIG. 19 shows the WVD of the difference signal $x_D(t)$, frequency in Hertz versus time in milliseconds.
Figure 20:
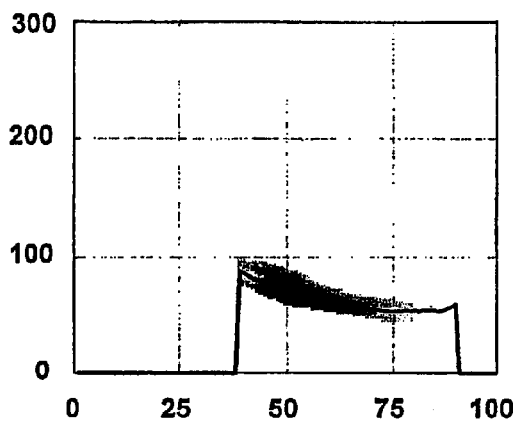
FIG. 20 shows the WVD of the difference signal $x_D(t)$, frequency in Hertz versus time in milliseconds, with a theoretical and estimated instantaneous frequency function of $P_2(t)$ signal superimposed.

An example of a digitized $S_2(t)$ signal with overlapping $A_2(t)$ and $P_2(t)$ components and background noise is presented in FIG. 12. The procedure developed for extracting overlapping $A_2(t)$ and $P_2(t)$ from $S_2(t)$ signals is performed in two steps, as illustrated in FIGS. 12 through 17 and 18 through 23, respectively, using the nonlinear transient chirp modeling approach described previously. Since $A_2(t)$ appears before $P_2(t)$, its instantaneous frequency (IF) is estimated first by computing the WVD of $S_2(t)$ as shown in FIG. 13. A masking operation, which is a filtering step, is then applied to extract the first most dominant ridge of $S_2(t)$ both in time and frequency corresponding to the time-frequency trajectory of $A_2(t)$. The masking operation serves to remove the cross-terms, the $P_2(t)$ component and any background noise and is illustrated in FIG. 14. Following application of the masking operation to the WVD of $S_2(t)$, the isolated energy ridge is used to estimate the time-frequency trajectory of the IF function of $A_2(t)$ shown as the black line superimposed on the Wigner-ville distribution of $A_2(t)$. of FIG. 14, by computing the first moment of the masked distribution with the equation (7). The phase function of $A_2(t)$ is then computed using equation (8) and the analytical form of the signal is generated using the Hilbert transform. The analytical signal is multiplied by the term $\exp(-j\phi_A(t))$ and low-pass filtered with a cut-off frequency determined by the bandwidth of its first most dominant lobe, see FIG. 15. The resulting $A_2(t)$ envelope, shown in FIG. 16, is then used to synthesize the $A_2(t)$ signal, shown in FIG. 17, which is subtracted from the $S_2(t)$ signal, shown in FIG. 12. The resulting difference signals, shown in FIG. 18, contains the $P_2(t)$ component, the background noise, and a residual $A_2(t)$ error signal, not correlated with $A_2(t)$, resulting from the $A_2(t)$ dechirping operation. The extraction of the $P_2(t)$ component is performed using a similar approach, see FIGS. 18 through 23, by applying nonlinear transient chirp modeling to the difference signal $X_D(t)$, as shown in FIG. 18.

A pig model was selected for experimental studies for validating the signal acquisition and processing methods. Pigs and humans have similar cardiovascular, pulmonary, and metabolic physiology. Pulmonary hypertension was induced in these animals by intravenous infusion of a thromboxane analogue which causes marked vasoconstriction of the pulmonary vessels. High-fidelity PAP measurements were performed using a 7F Millar catheter, Model Mikro-tip, SPR-598, inserted into the left jugular vein and flow-directed into the main pulmonary artery. The micromanometer was calibrated using a mercury column apparatus. A PCG microphone was positioned on the surface of the thorax at the pulmonary area to record the thoracic PCG. An ECG was also captured, amplified and digitized in a similar way to simplify the analysis of the PCG and the calculation of the cardiac interval. The high-fidelity PAP, ECG and PCG were digitized at a rate of 1000 samples per second by a data acquisition system installed in a personal computer as illustrated in FIG. 1.

Figure 9:
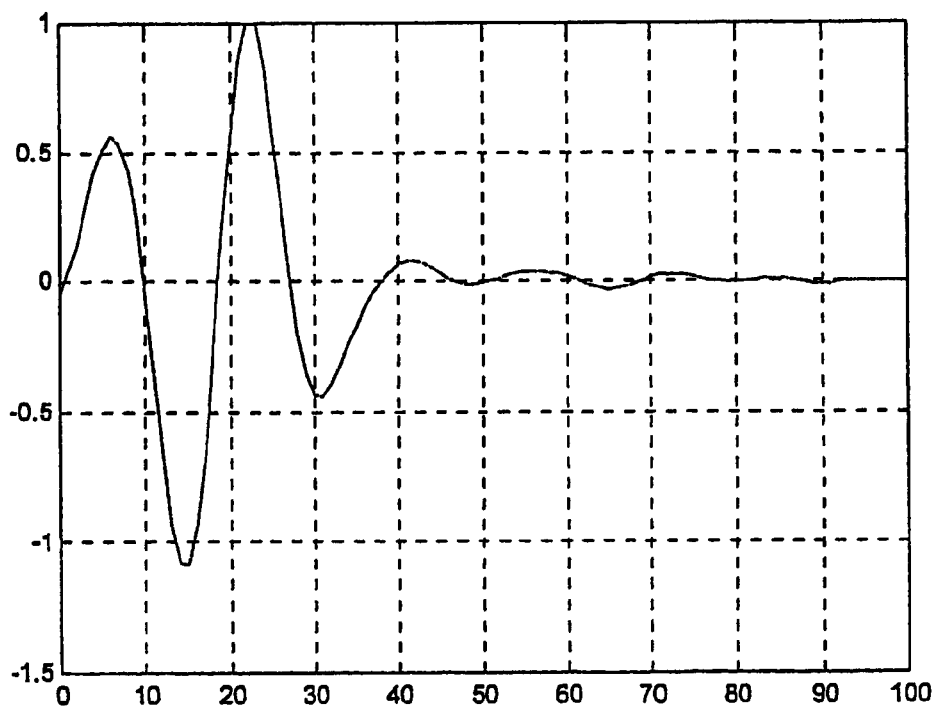
FIG. 9 is the cross-correlation function between the $A_2(t)$ and $P_2(t)$ components of FIG. 8, amplitude versus time in milliseconds.

The ECG, PCG and PAP were recorded in 15 animals and the splitting interval between $A_2(t)$ and $P_2(t)$ calculated for 59 different PCG recordings. When there was overlap between $A_2(t)$ and $P_2(t)$, the dechirping approach described previously was applied to ensure efficient identification and extraction of $A_2(t)$ and $P_2(t)$ from $S_2(t)$. The $A_2(t)$–$P_2(t)$ splitting interval (SI) was calculated by computing the cross-correlation function between $A_2(t)$ and $P_2(t)$, as shown in FIG. 9, and measuring the time of occurrence of its maximum amplitude. SI was then normalized (NSI) for heart rate as follows: NSI=(SI×100)/(duration of the cardiac cycle). The duration of the cardiac cycle was obtained by computing the interval between 10 consecutive QRS waves of the ECG. It could also be estimated by computing the mean interval between a series of consecutive $S_1(t)$ or $S_2(t)$ of the PCG.

Figure 10:
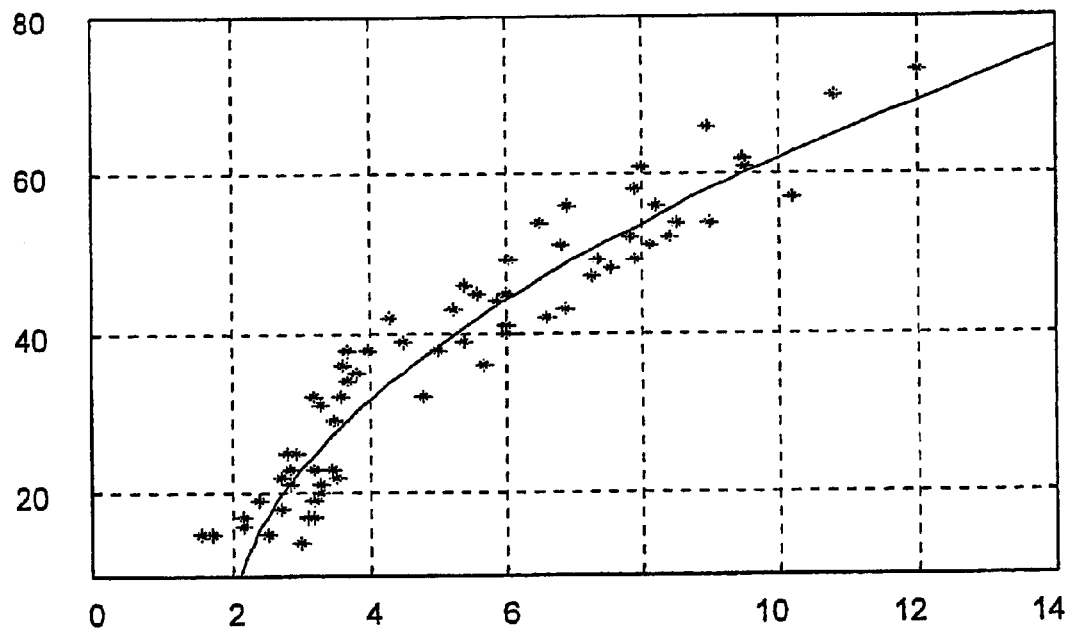
FIG. 10 is a graphic illustrating the relationship between the systolic pulmonary artery pressure and normalized splitting interval (NSI).
Figure 11:
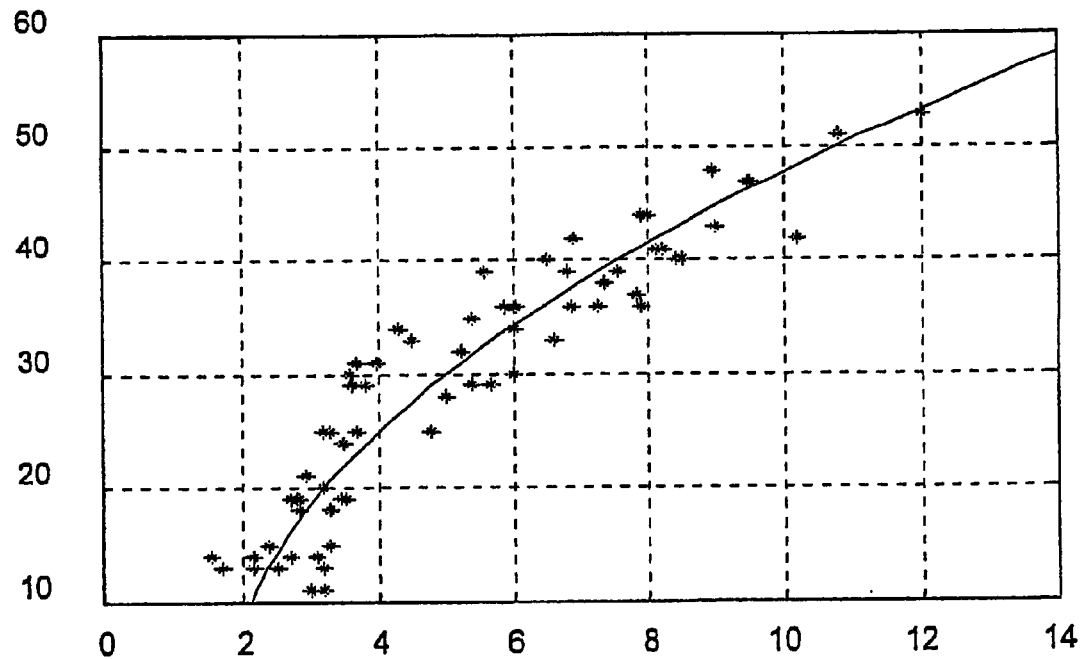
FIG. 11 is a graphic illustrating the relationship between the mean pulmonary artery pressure and the normalized splitting interval (NSI).

The measurement of SI was feasible in 88% of the recordings. A non linear regressive analysis was used to study the relationship between the normalized NSI and PAP. First, a curve-fitting procedure was performed to determine the curve that provides the best fit with the data collected in pigs. Second, the coefficient of determination (r) and the standard error of the estimate (SEE) were used to assess the goodness of fit between the optimal regressive curve and the data. The results of this statistical analysis showed that there was a strong relationship between the normalized SI (NSI) and systolic PAP, r=0.95 and SEE=±4.6 mmHg, as shown in FIG. 10 or mean PAP, r=0.93 and SEE=±3.6 mmHg, as shown in FIG. 11. These relationships are described by equations (2) and (3) when the model includes systolic or mean PAP, respectively. Moreover, the values of NSI obtained with this pig model, normal PAP: 3.3±0.4%, moderate pulmonary hypertension: 5.6±0.8%, and severe hypertension: 8.2±1.2%, were very consistent with those found in humans as shown by Leung et al. "Analysis of the second heart sound for diagnosis of paediatric heart disease," *IEEE Proceedings Sci Meas Technol*, vol. 145, no. 6, pp. 285–290, 1998 where normal subjects measured 3.3±1.8% and patients with diseases causing pressure or volume overload of the right ventricle measured 5.7±1.0%. Accordingly we believe that these equations are directly applicable to humans. This is the first experimental demonstration that NSI can provide an accurate quantitative estimate of the systolic and mean PAP and, moreover, this parameter is relatively independent of heart rate and systemic arterial pressure.

The second part of the experimental study was dedicated to the study of the relationship between the spectrum of $P_2(t)$ and the mean and systolic PAP. The mean resonant frequency (Fp) of $P_2(t)$ was determined by computing the power spectrum of $P_2(t)$ when $P_2(t)$ was well separated from $A_2(t)$, or of the dechirped $P_2(t)$ component when there was overlap between $A_2(t)$ and $P_2(t)$. A moderate correlation was found between Fp and systolic PAP, r=0.47 and SEE=±11.9 mmHg, or mean PAP, r=0.50 and SEE=±8.8 mmHg. This low correlation level was due to the large variability observed from one animal to another. With regards to the quality factor (Q) of $P_2(t)$, there was only a weak correlation with the PAP, r<0.25. This poor performance of Q appears to be related to its dependence on the amplitude of $P_2(t)$ and the mechanical coupling between the microphone and the thorax which are parameters highly variable from one animal to another. We have thus concluded that the spectral approach using Fp and Q to estimate the mean or systolic PAP was not suitable as such for a patent application but would require further study and experiment in order to determine the other anatomical and physiological factors which influence these relationships.

We claim:

1. Method of estimating systolic and mean pulmonary artery pressures of a patient, comprising the steps of:

(a) producing an electric signal $x_s(t)$ representative of heart sounds of the patient;

(b) extracting second heart sound $S_2(t)$ from the signal produced in step (a);

(c) extracting pulmonary and aortic components $P_2(t)$ and $A_2(t)$ from $S_2(t)$;

(d) extracting a signal representative of mean cardiac interval from the signal produced in step (a);

(e) correlating the pulmonary and aortic components $P_2(t)$ and $A_2(t)$ to obtain a cross correlation function;

(f) measuring a splitting interval as the time of occurrence of the maximal value of the cross correlation function obtained in step (e);

(g) producing a normalized splitting interval by dividing the splitting interval obtained in step (f) by the mean cardiac interval obtained in step (d); and (h) estimating the systolic and mean pulmonary artery pressures using of predetermined regressive functions, said predetermined regressive functions describing relationships between the normalized splitting interval and the systolic and mean pulmonary artery pressures.

2. Method according to claim 1, wherein the extracting of the pulmonary and aortic components $P_2(t)$ and $A_2(t)$ from $S_2(t)$ in step (c) comprises the steps of:

(i) determining a Wigner-Ville distribution $W_s(t,f)$ in view of time t and frequency f of the signal $S_2(t)$ produced in step (b) using the following function:

$$W_S(t,f) = \int_{-\infty}^{\infty} S_2\left(t + \frac{\tau}{2}\right) \cdot S_2^*\left(t - \frac{\tau}{2}\right) \cdot e^{-j2\pi f \tau} d\tau;$$

(ii) filtering $W_s(t,f)$ obtained in step (i) by means of the following function to obtain a masked time frequency representation $m_A(t,f)$ of the aortic component $A_2(t)$:

$$M_A(t,f) = W_s(t,f) \cdot \text{Mask}(t,f)$$

where Mask(t,f) is set to 1.0 around a first most dominant ridge, both in time and frequency, of $W_s(t,f)$, and 0.0 elsewhere;

(iii) determining the instantaneous frequency function $I_A(t)$ of the aortic component $A_2(t)$ using the following function:

$$I_A(t) = \frac{\int f \cdot m_A(t,f) df}{\int m_A(t,f) df};$$

(iv) determining a phase function $\phi_A(t)$ of the aortic component $A_2(t)$ using the following function:

$$\varphi_A(t) = \int_{-\infty}^{t} I_A(t) dt;$$

(v) determining a low-frequency amplitude envelope $A_A(t)$ corresponding to the aortic component $A_2(t)$ using the following steps:

(A) determining an analytical form $S_{2C}(t)$ of the signal $S_2(t)$ using of the following function:

$$S_{2C}(t) = S_2(t) + j \cdot S_{2H}(t)$$

where $S_{2H}(t)$ is the Hilbert Transform of $S_2(t)$;

(B) multiplying $S_{2C}(t)$ by $\exp(-j\phi_A(t))$ to obtain $S_{2C}(t) \cdot \exp(-j\phi_A(t))$;

(C) low-pass filtering the signal obtained in step(v) (B);

(vi) determining the aortic component $A_2(t)$ using the following function:

$$A_2(t) = A_A(t) \sin(\phi_A(t))$$

(vii) subtracting signal $A_2(t)$ obtained in step (vi) from signal $S_2(t)$ obtained in step (b) to obtain a difference signal $x_D(t)$;

(viii) determining a Wigner-Ville distribution $W_D(t,f)$ in view of time t and frequency f of the difference signal $x_D(t)$ using the following function:

$$W_D(t,f) = \int_{-\infty}^{\infty} x_D\left(t + \frac{\tau}{2}\right) \cdot x_D^*\left(t - \frac{\tau}{2}\right) \cdot e^{-j2\pi f \tau} d\tau;$$

(ix) filtering $W_D(t,f)$ obtained in step (viii) using the following function to obtain a masked time frequency representation $m_P(t,f)$ of the pulmonary component $P_2(t)$:

$$m_P(t,f) = W_D(t,f) \cdot \text{Mask}(t,f)$$

where Mask(t,f) is set to 1.0 around the most dominant ridge, both in time and frequency, of $W_D(t,f)$, and 0.0 elsewhere;

(x) determining the instantaneous frequency function $I_p(t)$ of the pulmonary component $P_2(t)$ using the following function:

$$I_p(t) = \frac{\int f \cdot m_P(t, f) df}{\int m_P(t, f) df};$$

(xi) determining the phase function $\phi_P(t)$ of the pulmonary component $P_2(t)$ according to the function:

$$\varphi_P(t) = \int_{-\infty}^{t} I_P(t) dt;$$

(xii) determining a low-frequency amplitude envelope $A_P(t)$ corresponding to the pulmonary component $P_2(t)$ using the following steps:
(A) determining an analytical form $x_{DH}(t)$ of the signal $x_D(t)$ using the following function:

$$x_{DC}(t) = x_D(t) + j x_{DH}(t)$$

where $x_{DH}(t)$ is the Hilbert transform of $x_D(t)$;
(B) multiplying $x_{DC}(t)$ by $\exp(-j\phi_P(t))$ to obtain $x_{DC}(t) \cdot \exp(-j\phi_P(t))$;
(C) low-pass filtering the signal obtained in step (xii) (B); and (xiii) determining the pulmonary component $P_2(t)$ by means of the following function:

$$P_2(t) = A_P(t) \cdot \sin(\phi_P(t)).$$

3. Method according to claim 2 wherein the low-pass filtering in step (v) (C) has a cut-off frequency selected within the range of 16 to 64 Hz and the low-pass filtering in step (xii) (C) has a cut-off frequency selected within the range of 16 to 64 Hz.

4. Method according to claim 3 where determining the cut-off frequency of the low-pass filter in step (v) (C) comprises the steps of:
(1) transforming the $S_2(t)$ signal into frequency domain using a Discrete Fourier Transform to obtain a transform;
(2) determining a power spectrum of the transform obtained in step (1);
(3) determining a main-low frequency energy lobe of the power spectrum;
(4) determining the cut-off frequency as a frequency corresponding to 5% of energy of the main-low frequency energy lobe;
(5) determining frequency bins of the $S_2(t)$ signal using a Discrete Fourier Transform;
(6) multiplying real and imaginary parts of frequency bins which are below the cut-off frequency by 1.00;
(7) multiplying real and imaginary parts of the of a frequency bin corresponding to the cut-off frequency by 0.70;
(8) multiplying real and imaginary parts of the of a first frequency bin above the cut-off frequency by 0.20;
(9) multiplying real and imaginary parts of the of a second frequency bin above the cut-off frequency by 0.02;
(10) multiplying real and imaginary parts of all other of frequency bins which are above the cut-off frequency of the low pass filter by 0.00; and
(11) applying inverse Discrete Fourier Transform to the results of steps 6, 7, 8, 9 and 10 to obtain representations in the time domain.

5. Method according to claim 3 where determining the cut-off frequency of the low-pass filter in step (xii) (C) comprises the steps of:
(1) transforming the difference signal $X_D(t)$ into frequency domain using a Discrete Fourier Transform to obtain a transform;
(2) determining a power spectrum of the transform obtained in step (1);
(3) determining a main-low frequency energy lobe of the power spectrum;
(4) determining the cut-off frequency as a frequency corresponding to 5% of energy of the main-low frequency energy lobe;
(5) determining frequency bins of the difference signal $X_D(t)$ using a Discrete Fourier Transform;
(6) multiplying real and imaginary parts of frequency bins which are below the cut-off frequency by 1.00;
(7) multiplying real and imaginary parts of a frequency bin corresponding to the cut-off frequency by 0.70;
(8) multiplying real and imaginary parts of the of a first frequency bin above the cut-off frequency by 0.20;
(9) multiplying real and imaginary parts of the of a second frequency bin above the cut-off frequency by 0.02;
(10) multiplying the real and imaginary parts of all other of the frequency bins which are above the cut-off frequency of the low pass filter by 0.00; and
(11) applying inverse Discrete Fourier Transform to the results of steps 6, 7, 8, 9 and 10 to obtain representations in the time domain.

6. Method according to claim 1 where the predetermined regressive functions have the form:

$$x = a + by^{1/n},$$

said function describing the relationship between the normalized splitting interval y and the systolic and mean pulmonary artery pressures, x, by means of predetermined constants a, b and n.

7. Apparatus for estimating systolic and mean pulmonary artery pressures of a patient, comprising:
first producing means for producing an electric signal $x_S(t)$ representative of heart sounds of the patient;
first extracting means for extracting second heart sound $S_2(t)$ from the signal produced by the first producing means;
second extracting means for extracting pulmonary and aortic components $P_2(t)$ and $A_2(t)$ from $S_2(t)$ extracted by the first extracting means;
third extracting means for extracting a signal representative of mean cardiac interval from the signal produced by the first producing means;
correlating means for correlating the pulmonary and aortic components $P_2(t)$ and $A_2(t)$ to obtain a cross correlation function;
measuring means for measuring a splitting interval as the time of occurrence of the maximal value of the cross correlation function obtained by the correlating means;
second producing means for producing a normalized splitting interval by dividing the splitting interval obtained from the measuring means by the mean cardiac interval obtained from the third extracting means; and estimating means for estimating the systolic and mean pulmonary artery pressures by means of predetermined regressive functions said predetermined regressive functions describing relationships between the normalized splitting interval and the systolic and mean pulmonary artery pressures.

8. Apparatus according to claim 7, wherein the second extracting means for extracting the pulmonary and aortic components $P_2(t)$ and $A_2(t)$ from $S_2(t)$ comprises:

first determining means for determining a Wigner-Ville distribution $W_S(t,f)$ in view of time t and frequency f of the signal $S_2(t)$ extracted by the first extracting means using the following function:

$$W_S(t, f) = \int_{-\infty}^{\infty} S_2\left(t+\frac{\tau}{2}\right) \cdot S_2^*\left(t-\frac{\tau}{2}\right) \cdot e^{-j2\pi f\tau} d\tau;$$

first filtering means for filtering $W_S(t,f)$ obtained from the first determining means using the following function to obtain a masked time frequency representation $m_A(t,f)$ of the aortic component $A_2(t)$:

$$m_A(t,f) = W_S(t,f) \cdot \text{Mask}(t,f)$$

where Mask(t,f) is set to 1.0 around a first most dominant ridge, of $W_S(t,f)$, and 0.0 elsewhere;

second determining means for determining the instantaneous frequency function $I_A(t)$ of the aortic component $A_2(t)$ using the following function:

$$I_A(t) = \frac{\int f \cdot m_A(t, f) df}{\int m_A(t, f) df};$$

third determining means for determining a phase function $\phi_A(t)$ of the aortic component $A_2(t)$ using the following function:

$$\varphi_A(t) = \int_{-\infty}^{t} I_A(t) dt;$$

fourth determining means for determining a low-frequency amplitude envelope $A_A(t)$ corresponding to the aortic component $A_2(t)$, said fourth determining means comprising:

determining means for determining an analytical form $S_{2C}(t)$ of the signal $S_2(t)$ using the following function:

$$S_{2C}(t) = S_2(t) + j \cdot S_{2H}(t)$$

where $S_{2H}(t)$ is the Hilbert Transform of $S_2(t)$;
multiplying means for multiplying $S_{2C}(t)$ by $\exp(-j\phi_A(t))$ to obtain $S_{2C}(t) \cdot \exp(-j\phi_A(t))$;
filtering means for low-pass filtering the signal obtained from the multiplying means;

fifth determining means for determining the aortic component $A_2(t)$ using the function:

$$A_2(t) = A_A(t) \cdot \sin(\phi_A(t));$$

subtracting means for subtracting the signal $A_2(t)$ obtained by the fifth determining means from signal $S_2(t)$ obtained from the first extracting means to obtain a difference signal $x_D(t)$;

sixth determining means for determining a Wigner-Ville distribution $W_D(t,f)$ in view of time t and frequency f of the difference signal $x_D(t)$ by means of the following function:

$$W_D(t, f) = \int_{-\infty}^{\infty} x_D\left(t+\frac{\tau}{2}\right) \cdot x_D^*\left(t-\frac{\tau}{2}\right) \cdot e^{-j2\pi f\tau} d\tau;$$

Second filtering means for filtering $W_D(t,f)$ obtained from the sixth determining means by using the following function to obtain a masked time frequency representation $m_P(t,f)$ of the pulmonary component $P_2(t)$:

$$m_P(t,f) = W_D(t,f) \cdot \text{Mask}(t,f)$$

where Mask(t,f) is set to 1.0 around the most dominant ridge of $W_D(t,f)$, and 0.0 elsewhere;

seventh determining means for determining the instantaneous frequency function $I_P(t)$ of the pulmonary component $P_2(t)$ by using the function:

$$I_P(t) = \frac{\int f \cdot m_P(t, f) df}{\int m_P(t, f) df};$$

eighth determining means for determining the phase function $\phi_P(t)$ of the pulmonary component $P_2(t)$ by using the function:

$$\varphi_P(t) = \int_{-\infty}^{t} I_P(t) dt;$$

ninth determining means for determining a low-frequency amplitude envelope $A_P(t)$ corresponding to the pulmonary component, said ninth determining means comprising:

tenth determining means for determining an analytical form $x_{DH}(t)$ of the signal $x_D(t)$ using the function:

$$x_{DC}(t) = x_D(t) + j x_{DH}(t)$$

where $x_{DH}(t)$ is the Hilbert transform of $x_D(t)$;
multiplying means for multiplying $x_{DC}(t)$ by $\exp(-j\phi_P(t))$ to obtain $x_{DC}(t) \cdot \exp(-j\phi_P(t))$;
filtering means for low-pass filtering the signal obtained from the multiplying means; and
eleventh determining means for determining the pulmonary component $P_2(t)$ by using the following function:

$$P_2(t) = A_P(t) \cdot \sin(\phi_P(t)).$$

9. Apparatus according to claim 8 where the predetermined regressive functions have the form:

$$x = a + by^{1/n},$$

said function describing the relationship between the normalized splitting interval y and the systolic and mean pulmonary artery pressures, x, by means of predetermined constants a, b and n.

* * * * *